US008382479B2

(12) United States Patent
Navarro

(10) Patent No.: US 8,382,479 B2
(45) Date of Patent: Feb. 26, 2013

(54) APPARATUS AND METHOD FOR REMOVING ENAMEL FROM A PERSON'S TOOTH

(76) Inventor: Carlos F. Navarro, Dallas, TX (US)

(*) Notice: Subject to any disclaimer, the term of this patent is extended or adjusted under 35 U.S.C. 154(b) by 0 days.

(21) Appl. No.: 13/016,219

(22) Filed: Jan. 28, 2011

(65) Prior Publication Data

US 2011/0136074 A1    Jun. 9, 2011

Related U.S. Application Data

(63) Continuation of application No. 12/011,548, filed on Jan. 28, 2008, now Pat. No. 7,878,807, which is a continuation of application No. 11/225,485, filed on Sep. 13, 2005, now Pat. No. 7,322,822.

(60) Provisional (Continued)

(51) Int. Cl.
    A61C 5/00    (2006.01)
(52) U.S. Cl. ......................... 433/215; 433/166
(58) Field of Classification Search .................. 433/125, 433/142, 166, 215
    See application file for complete search history.

(56) References Cited

U.S. PATENT DOCUMENTS

| 3,624,908 A | 12/1971 | Ricketts et al. |
| 4,109,384 A | 8/1978 | Dorian |
| 4,270,556 A | 6/1981 | McAllister |
| 4,483,676 A | 11/1984 | Thierman |
| 4,505,678 A | 3/1985 | Andersson |
| 4,563,152 A | 1/1986 | McClure |
| 4,830,615 A | 5/1989 | Goldstein et al. |
| 4,976,625 A | 12/1990 | Weissman |
| 5,040,977 A | 8/1991 | Weissman |
| 5,376,444 A | 12/1994 | Grotepass et al. |
| 5,476,381 A | 12/1995 | Dragan |
| 5,505,617 A | 4/1996 | Skeppmark et al. |
| 5,579,786 A * | 12/1996 | Wolk et al. .................... 132/322 |
| 5,613,300 A | 3/1997 | Schmidt |
| 6,025,076 A | 2/2000 | Collins |

(Continued)

FOREIGN PATENT DOCUMENTS

| DE | 3415450 | 10/1984 |
| WO | WO 2004/073538 | 9/2004 |

(Continued)

OTHER PUBLICATIONS

PCT/US05/32415, Notification of Transmittal of the International Search Report and the Written Opinion of the International Searching Authority, or the Declaration, 7 pages, mailed Sep. 6, 2006.

(Continued)

Primary Examiner — Cris L Rodriguez
Assistant Examiner — Eric Rosen
(74) Attorney, Agent, or Firm — Baker Botts L.L.P.

(57) ABSTRACT

According to one embodiment, an apparatus for removing enamel from a person's tooth includes a blade portion and a handle portion. The blade portion includes an abrasive surface adapted to remove enamel from the tooth in response to reciprocating movement of the abrasive surface against the enamel of the tooth. The handle portion is coupled to the blade portion, has a substantially solid cross-section, and is adapted to be inserted into a corresponding opening in a driver mechanism that is adapted to drive reciprocating movement of the blade portion to provide the reciprocating movement of the abrasive surface.

17 Claims, 4 Drawing Sheets

Related U.S. Application Data application No. 60/609,518, filed on Sep. 13, 2004, provisional application No. 60/635,647, filed on Dec. 13, 2004, provisional application No. 60/683,623, filed on May 23, 2005.

U.S. PATENT DOCUMENTS

| | | | |
|---|---|---|---|
| 6,241,522 | B1 | 6/2001 | Schon et al. |
| 6,247,931 | B1 | 6/2001 | Postal et al. |
| 6,267,594 | B1 * | 7/2001 | Hugo .............................. 433/119 |
| 6,508,649 | B2 | 1/2003 | Gratz |
| 6,736,639 | B1 | 5/2004 | Summer |
| 6,780,013 | B2 | 8/2004 | Kubein-Meesenburg et al. |
| 6,925,719 | B2 | 8/2005 | Callne |
| 7,131,840 | B2 | 11/2006 | Constantino |
| 7,322,822 | B2 * | 1/2008 | Navarro .......................... 433/125 |
| 7,348,046 | B2 | 3/2008 | Liedloff et al. |
| 7,758,343 | B1 | 7/2010 | Navarro |
| 7,878,807 | B2 | 2/2011 | Navarro |
| 2002/0069592 | A1 | 6/2002 | Sherman et al. |
| 2003/0022131 | A1 | 1/2003 | Kangasniemi et al. |
| 2003/0228554 | A1 | 12/2003 | Brown |
| 2004/0091839 | A1 | 5/2004 | Fischer |
| 2005/0058963 | A1 | 3/2005 | Stockstill |
| 2005/0115085 | A1 | 6/2005 | Caline |
| 2006/0057540 | A1 | 3/2006 | Navarro |
| 2006/0063131 | A1 | 3/2006 | Kim |
| 2008/0081313 | A1 | 4/2008 | Kim |
| 2008/0131839 | A1 | 6/2008 | Navarro |
| 2008/0172951 | A1 | 7/2008 | Starling |
| 2010/0178633 | A1 | 7/2010 | Navarro |
| 2011/0081830 | A1 | 4/2011 | Pollasky |

FOREIGN PATENT DOCUMENTS

| | | |
|---|---|---|
| WO | WO 2006/031728 | 9/2005 |

OTHER PUBLICATIONS

PCT Notification of Transmittal of the International Search Report and the Written Opinion of the International Searching Authority, or the Declaration, PCT/US2009/068039, 16 pages, mailed Apr. 8, 2010.

PCT/US2005/032415, Notification Concerning Transmittal of International Preliminary Report on Patentability (Chapter 1 of the Patent Cooperation Treaty); 5 pages, mailed Mar. 22, 2007.

Supplementary European Search Report; Application No. EP 06 79 6519; 6 pages, Jan. 16, 2009.

Canada Intellectual Property, Office Action App. No. 2,577,155, 2 pages, Jul. 7, 2010.

Carlos F. Navarro; "*Apparatus and Method for Removing Enamel From a Person's Tooth;*" U.S. Appl. No. 11/225,485; 22 pages, filed Sep. 13, 2005.

Carlos F. Navarro; "*Apparatus and Method for Removing Enamel From a Person's Tooth;*" Patent Application Serial PCT/US05/32415; 39 pages, filed Sep. 13, 2005.

Carlos F. Navarro; "*Apparatus and Method for Removing Enamel From a Person's Tooth;*" U.S. Appl. No. 12/011,548; 21 pages, filed Jan. 28, 2008.

Carlos F. Navarro; "*Apparatus and Method for Removing Enamel From a Person's Tooth;*" U.S. Appl. No. 12/354,107; 28 pages, filed Jan. 15, 2009.

Canadian Intellectual Property Office, Office Action, Application No. 2,577,155, Carlos Navarro, 2 pages, Jul. 20, 2011.

* cited by examiner

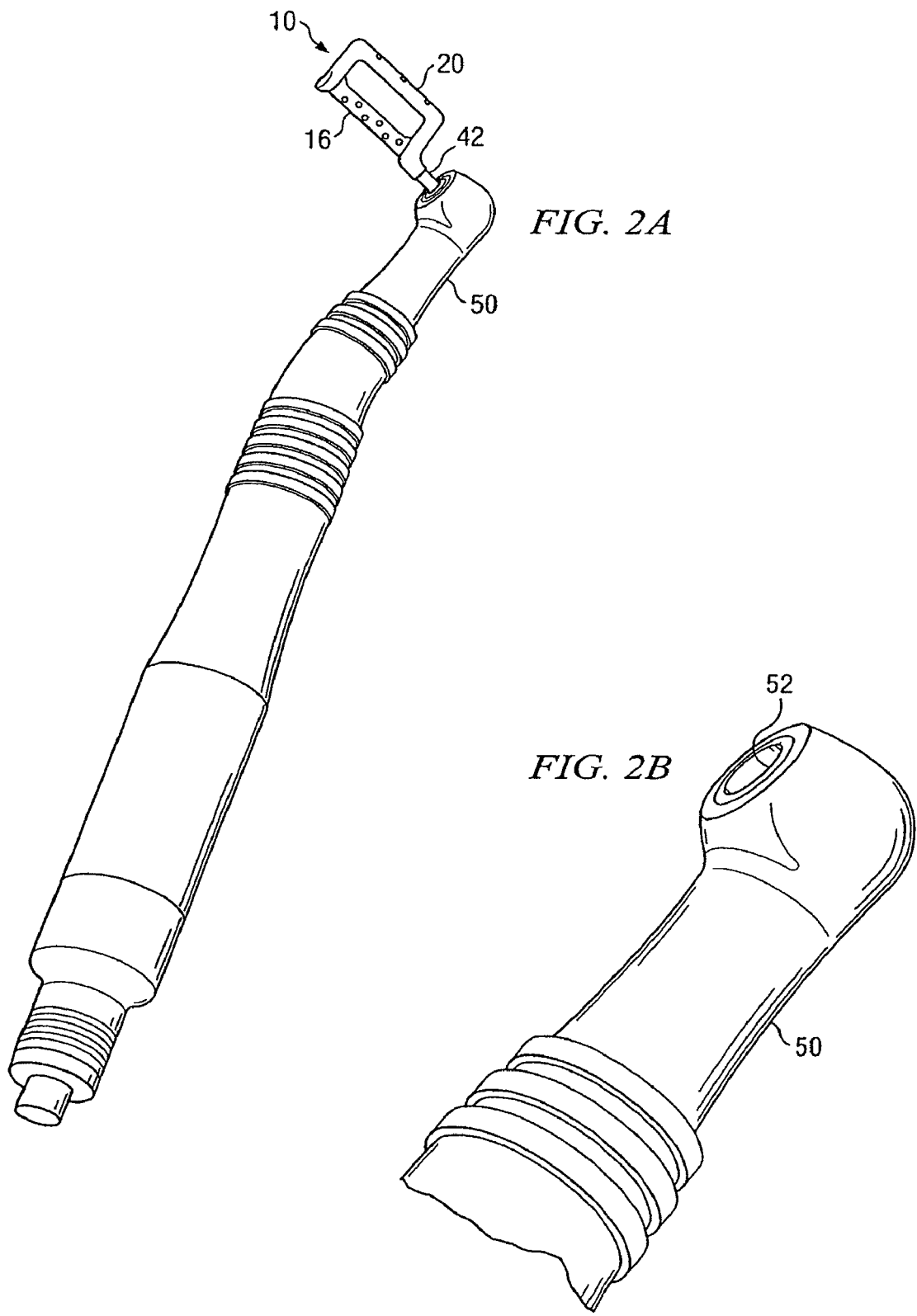

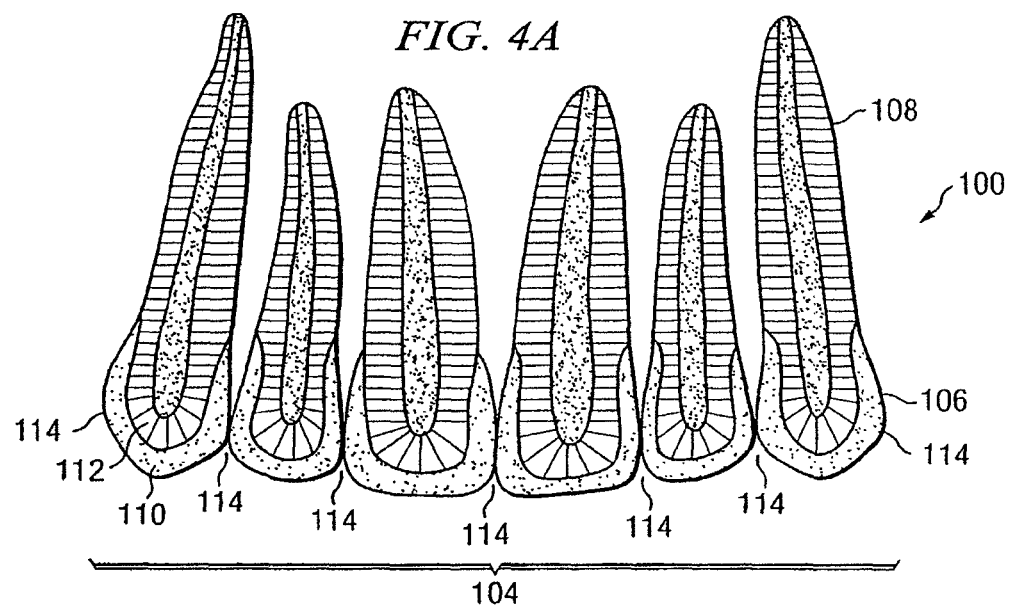
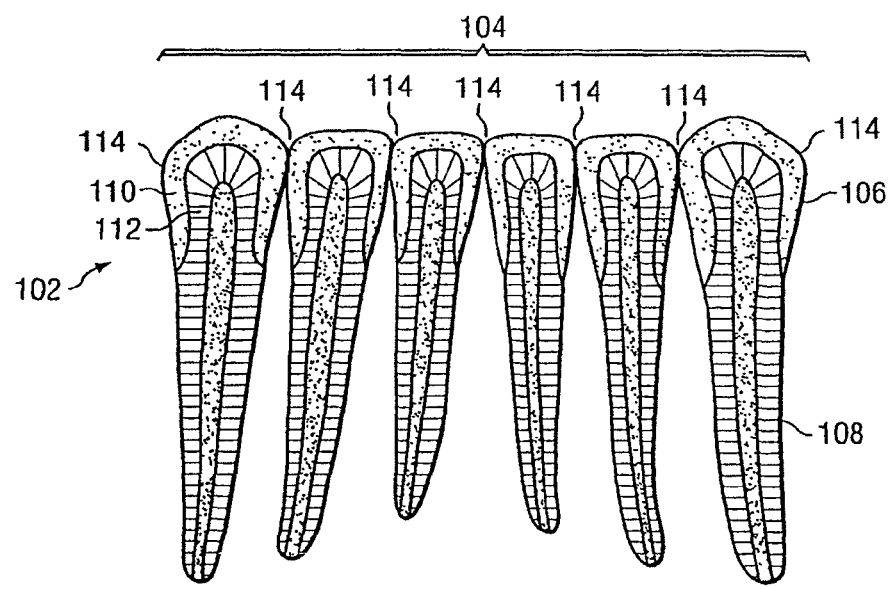

APPARATUS AND METHOD FOR REMOVING ENAMEL FROM A PERSON'S TOOTH

RELATED APPLICATIONS

This application is a continuation of U.S. application Ser. No. 12/011,548 filed Jan. 28, 2008, now U.S. Pat. No. 7,878,807, which is a continuation of U.S. application Ser. No. 11/225,485 filed Sep. 13, 2005, entitled "Apparatus and Method for Removing Enamel from a Person's Tooth," now U.S. Pat. No. 7,322,822, which claims the benefit under 35 U.S.C. §119(e) of U.S. Provisional Application Ser. No. 60/609,518 filed Sep. 13, 2004, U.S. Provisional Application Ser. No. 60/635,647 filed Dec. 13, 2004, and U.S. Provisional Application Ser. No. 60/683,623 filed May 23, 2005.

TECHNICAL FIELD

This invention relates generally to dentistry and orthodontics and in particular to an apparatus and method for removing enamel from a person's tooth.

BACKGROUND

Many people experience adverse conditions resulting from the overcrowding of teeth associated with malocclusion. To avoid the need for one or more tooth extractions, such conditions have been treated effectively by removing enamel from one or more teeth in the person's mouth to create space or additional space. Interproximal Enamel Reduction (IER) is the clinical act of removing part of the enamel from an interproximal contact area of a person's tooth. To perform IER, an orthodontist or other clinical professional manually or mechanically files down the interproximal contact area of the tooth with a metallic strip or disk. Typically, over seven millimeters of space may be created between teeth in a person's upper arch, and over five millimeters of space may be created between teeth in a person's lower arch. In addition to creating space for orthodontic and other treatments, IER may be used to alter the size and shape of a person's teeth. Accordingly, IER often contributes to an improved finishing of orthodontic treatment and dental aesthetics. Because debris from the IER procedure accumulates around the interproximal contact area, the procedure must be interrupted and the interproximal contact area cleaned periodically during the procedure, adding to the length and cost of the procedure. Additionally, tools used for IER are typically constructed from multiple pieces of metal coupled together using welds, rivets, or other means and can be expensive. For economic reasons, these tools typically must be reused a number of times and therefore must be thoroughly cleaned and sterilized between IER procedures, further increasing costs associated with these procedures. Such tools are also typically constructed using molded sheet metal, which results in poor structural integrity, negatively impacting their ability to couple to an associated driver mechanism and reducing their useful life.

SUMMARY OF THE INVENTION

The apparatus and method of the present invention may reduce or eliminate certain problems and disadvantages associated with previous dental devices.

According to one embodiment, an apparatus for removing enamel from a person's tooth includes a blade portion and a handle portion. The blade portion includes an abrasive surface adapted to remove enamel from the tooth in response to reciprocating movement of the abrasive surface against the enamel of the tooth. The handle portion is coupled to the blade portion, has a substantially solid cross-section, and is adapted to be inserted into a corresponding opening in a driver mechanism that is adapted to drive reciprocating movement of the blade portion to provide the reciprocating movement of the abrasive surface.

Particular embodiments of the present invention may provide one or more technical advantages. According to the present invention, an apparatus and method are provided for removing enamel from one or more of a person's teeth. The removal of enamel from one or both of two adjacent teeth may create space, or additional space, between the adjacent teeth. Thus, an IER procedure may be performed to prevent or treat the overcrowding of teeth associated with malocclusion and avoid the need for one or more tooth extractions. Additionally or alternatively, an IER procedure may be used to recontour or otherwise alter the size and shape of one or more of the person's teeth to provide a more aesthetically pleasing result.

In certain embodiments, the apparatus includes a one-piece integrally-formed frame, preferably metal, that provides strength and rigidity and is unlikely to break or otherwise fail during use. In certain embodiments, portions of the frame, including at least the handle portion, are enveloped or otherwise covered by a body, which may be made of plastic and may also be integrally-formed. In certain embodiments, the resulting handle may be manually gripped by an orthodontist or other clinical professional when using the apparatus to remove enamel from a person's tooth. In certain embodiments, the apparatus is lightweight and may be easily positioned and manipulated by the clinical professional. In certain embodiments, a driver mechanism may be used in cooperation with the frame to drive reciprocal motion of the abrasive surface of the blade portion of the frame against the enamel of a person's tooth. In certain embodiments, one or more apertures formed through the blade portion of the frame channel debris away from the interproximal contact area as an IER procedure is being performed. As a result, bits of removed enamel, saliva, blood and any liquids, chemicals, or pastes used in the IER procedure and present at the interproximal contact area may be channeled away from the tooth through the one or more apertures and the area kept cleaner and visibly unobstructed during the procedure, reducing or eliminating the need to interrupt the procedure to clean the interproximal contact area. In certain embodiments, the apparatus may be inexpensively mass manufactured such that it is economically practical to dispose of the apparatus after a single use, eliminating the need for cleaning and sterilization between uses. In certain embodiments, the handle may have a substantially circular cross-section with a substantially continuous circumference. The handle may also be substantially solid. As a result, the handle may be substantially non-deformable such that cross-sectional dimensions of the handle remain substantially constant when the handle is force-fitted into or otherwise coupled to a corresponding opening of a driver mechanism.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

For a more complete understanding of the present invention and advantages thereof, reference is now made to the following description taken in conjunction with the accompanying drawings, in which:

FIGS. 2A and 2B illustrate an example driver mechanism adapted to coupled to an example apparatus for removing enamel;

FIGS. 4A and 4B illustrate example upper and lower arches of a person's mouth and example interproximal contact areas from which enamel may be removed.

DESCRIPTION OF EXAMPLE EMBODIMENTS

According to the present invention, an apparatus and method are provided for removing enamel from one or more of a person's teeth. The removal of enamel from one or both of two adjacent teeth may create space, or additional space, between the adjacent teeth. Thus, an IER procedure may be performed to prevent or treat the overcrowding of teeth associated with malocclusion and avoid the need for one or more tooth extractions. Additionally or alternatively, an IER procedure may be used to recontour or otherwise alter the size and shape of one or more of the person's teeth to provide a more aesthetically pleasing result.

Figure 1:
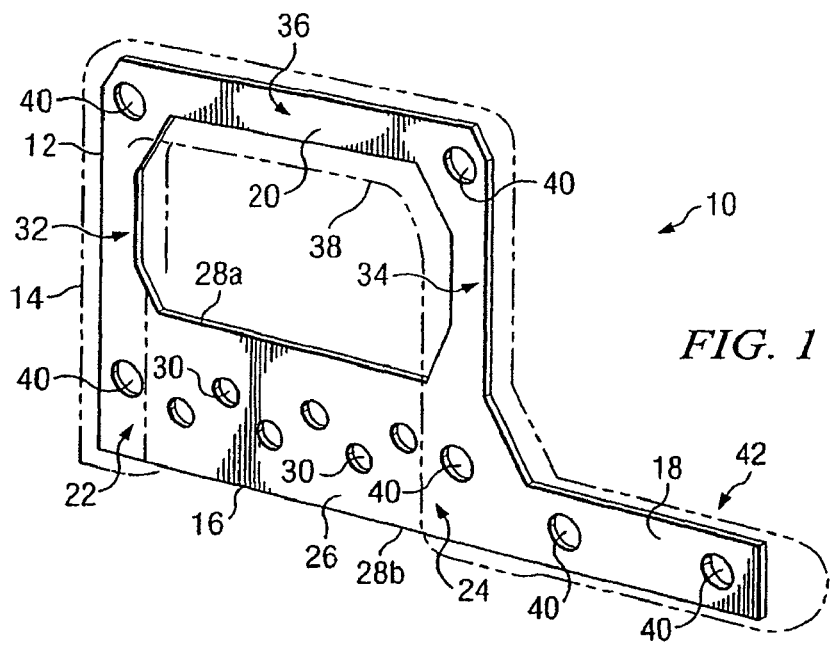
FIG. 1 provides a cut-away view of an example apparatus for removing enamel from a person's tooth.

FIG. 1 illustrates an example apparatus 10 for removing enamel from a person's tooth. Apparatus 10 includes a frame 12 and a body 14. In certain embodiments, frame 12 is a one-piece frame integrally-formed from a single piece of material. Frame 12 may be made of steel or another metal. Body 14 is formed around frame 12 to envelop or otherwise cover appropriate portions of frame 12. In certain embodiments, body 14 may be a one-piece body integrally-formed of plastic or another suitable material. Apparatus 10 is used to remove enamel from a person's tooth. For example, apparatus 10 may be used to remove enamel from one or both of two adjacent teeth in an IER procedure to create space, or additional space, between the adjacent teeth to prevent or treat overcrowding associated with malocclusion. As another example, apparatus 10 may be used to remove enamel from a tooth in an IER or other procedure to recontour the tooth to provide a more aesthetically pleasing shape. Accordingly, the recontouring of a tooth using apparatus 10 may contribute to an improved finish of orthodontic treatment. After portions of the enamel are removed at an interproximal contact area, the teeth may be polished and a protective treatment applied. The present invention contemplates any appropriate use of apparatus 10 according to particular needs.

In certain embodiments, frame 12 includes a blade portion 16, a handle portion 18, and a stabilizer portion 20. Blade portion 16 extends in a first direction from a first end 22 to a second end 24. Blade portion 16 includes one or more abrasive surfaces 26 adapted to remove enamel from a person's tooth when an abrasive surface 26 of blade portion 16 is repeatedly moved over, through, or otherwise against the enamel of the tooth. For example, abrasive surface 26 may be repeatedly advanced in generally opposing directions with respect to the person's tooth in a manner that causes abrasive surface 26 to gradually remove enamel from the tooth. Such movement is referred to herein as "reciprocating" movement. In certain embodiments, abrasive surface 26 may extend between two edges 28 of blade portion 16 and may be used to "file" or otherwise remove enamel from the person's tooth. In certain other embodiments, instead or in addition, abrasive surface 26 may lie along edge 28b of blade portion 16 and may be used to "saw" or otherwise remove enamel from the tooth.

In certain embodiments, blade portion 16 includes one or more apertures 30 for channeling debris away from the tooth. For example, apertures 30 may comprise substantially circular openings. As blade portion 16 is advanced against the tooth and enamel is gradually removed, the IER procedure may result in the accumulation of debris in and around the interproximal contact area. The accumulated debris may include, for example, bits of removed enamel, saliva, blood and any liquids, chemicals, or pastes used in the IER procedure. Apertures 30 of blade portion 16 may act to channel such debris away from the interproximal contact area such that abrasive surface 26 remains against the interproximal contact area for more accurate enamel removal. Additionally, the patient's mouth may be kept cleaner as the IER procedure is being performed, without undue interruption.

As described above, in certain embodiments frame 12 also includes handle portion 18 and stabilizer portion 20. Handle portion 18 extends from second end 24 of blade portion 16 in generally the same direction as abrasive surface 26. As described in greater detail below, handle portion 18 may be gripped manually or mechanically by a clinical professional to perform IER or any other suitable procedure. Stabilizer portion 20 operates to stabilize apparatus 10 during use. Although desirable for stability, the present invention contemplates apparatus 10 lacking stabilizer portion 20. In certain embodiments, stabilizer portion 20 is substantially U-shaped and includes a first portion 32, a second portion 34, and a third portion 36. First portion 32 may extend from first end 22 of blade portion 16 in a first direction that is generally perpendicular to the direction of abrasive surface 26. Second portion 34 of stabilizer portion 20 may extend from second end 24 of blade portion 16 in a second direction that is also generally perpendicular the direction of abrasive surface 26. Third portion 36 extends between and couples first portion 32 and second portion 34. Although a particular configuration of stabilizer portion 20 and its portions 32, 34, 36 with respect to blade portion 20 is primarily described, the present invention contemplates stabilizer portion 20 having any suitable configuration with respect to blade portion 20. Stabilizer portion 20 cooperates with blade portion 16 to define an opening 38. Similar to apertures 30 of blade portion 16, opening 38 may channel the debris away from the tooth as the IER or other procedure is being performed.

As described above, in certain embodiments apparatus 10 includes a one-piece integrally-formed body 14 that envelops or otherwise covers appropriate portions of frame 12. Body 14 may be formed of plastic. The plastic forming body 14 may include a mostly synthetic or semi-synthetic organic condensation or polymerization product that may be molded or extruded in the desired form. Accordingly, body 14 may be produced by a polymerization process that includes melting the polymer, placing frame 12 into a mold of the desired shape of body 14, allowing the melted polymer to envelop or otherwise cover appropriate portions of frame 12 inside the mold, and allowing the polymer to cool and harden to form body 14.

In certain embodiments, body 14 may fully or partially envelop or otherwise cover handle portion 18 and stabilizer portion 20, leaving at least a portion of abrasive surface 26 of blade portion 16 exposed. Additionally, the molding of body 14 around frame 12 may operate to couple body 14 to frame 12. In certain embodiments, frame 12 may include one or more apertures 40 through handle portion 18 and stabilizer portion 20. During the formation of body 14, the material forming body 14 may be allowed to flow through apertures 40 to improve the coupling of body 14 to frame 12. Although apertures 40 may facilitate the coupling of body 14 and frame 12, other suitable coupling mechanisms may additionally or alternatively couple body 14 to frame 12. For example, one or more rivets, screws, bolts, or other coupling mechanisms may couple body 14 to frame 12.

In certain embodiments, handle 42 may be grasped by an orthodontist or other clinical professional and used to manually position apparatus 10 proximate the interproximal contact area of a person's tooth. As a result, the clinical professional using apparatus 10 may supply and control the force and motion necessary to advance abrasive surface 26 of blade portion 16 in opposing directions against the tooth.

In certain embodiments, handle 42 may be configured to coupled to a driver mechanism. FIGS. 2A and 2B illustrate an example driver mechanism 50 adapted to couple to an example apparatus 10 for removing enamel from a person's tooth. Driver mechanism 50 may include a recess 52 adapted to receive and secure handle 42. For example, handle 42 may be force fitted into recess 52. As another example, handle 42 may be inserted into recess 52 and secured using a set screw or otherwise. Driver mechanism 50 may be operable to mechanically advance abrasive surface 26 in opposing directions against the tooth. As an example, driver mechanism 50 may be operable to mechanically move abrasive surface 26 in a substantially linear reciprocating motion. As another example, driver mechanism 50 may be operable to mechanically move abrasive surface 26 in a substantially elliptical reciprocating motion, with the elliptical path being in a plane substantially parallel to abrasive surface 26. For example, driver mechanism 50 may translate rotational movements, such as in a conventional dental drill, to reciprocating movements through appropriate gearing or other mechanisms. Such gearing or other mechanisms are well known to persons in the art. In certain embodiments, driver mechanism 50 may be configured to interchangeably receive and secure apparatus 10 and also other tools used in orthodontic or other clinical procedures. For example, driver mechanism 50 may be configured to also receive and secure a drill, polishing brush, or other tool.

In certain embodiments, handle 42 has a substantially circular cross-section with a substantially continuous circumference. As a result, handle 42 may be substantially non-deformable such that cross-sectional dimensions of handle 42 remain substantially constant when handle 42 is force-fitted into or otherwise coupled to recess 52 of driver mechanism 50. As shown in FIG. 1, handle 42 may be substantially solid in cross-section including a portion of frame 12 covered by a portion of body 14. Alternatively, handle 42 may be substantially solid in cross-section and formed solely by a portion of frame 12 or a metal, plastic, or other component coupled to frame 12. These embodiments may be distinguished from tools formed from molded sheet metal having thin-walled handles with C-shaped cross-sections. Such handles may be compressed and permanently or temporarily deformed when force-fitted into recess 52 of driver mechanism 50. Such deformation often results in changes to the cross-sectional dimensions that may prevent the tools from properly and securely coupling to driver mechanism 50, especially after a number of uses. After repeated uses, such deformation may lead to material fatigue and, ultimately, failure.

Figure 3A:
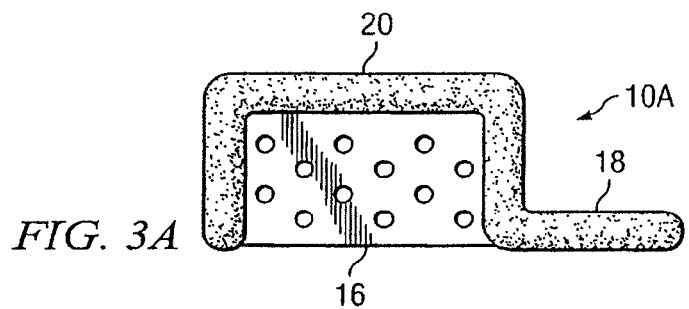
FIGS. 3A-3D illustrate examples of an apparatus for removing enamel from a person's tooth.
Figure 3B:
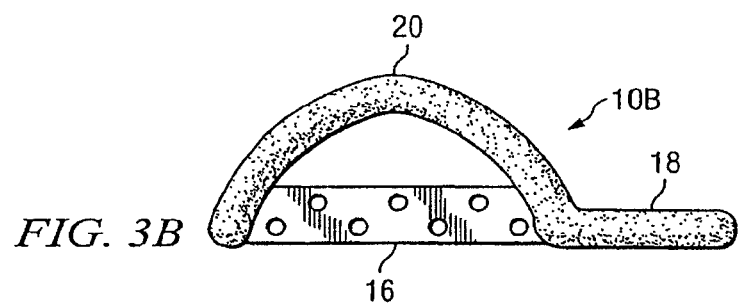
Figure 3C:
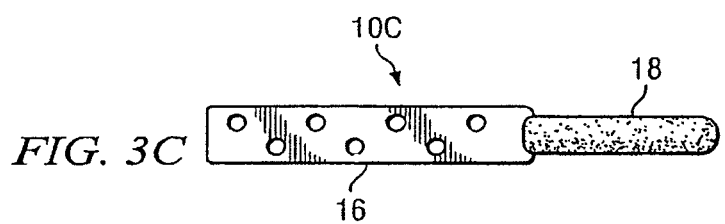
Figure 3D:
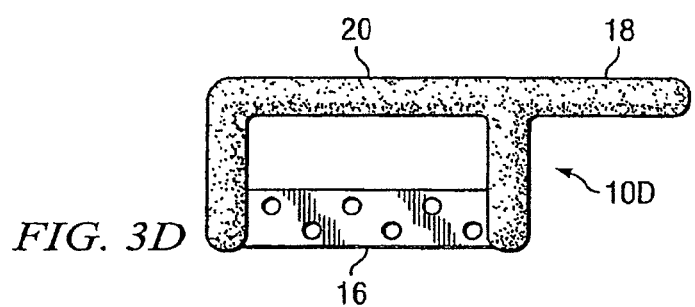

FIGS. 3A-3D illustrate examples of apparatus 10. As shown in FIG. 3A, in certain embodiments, blade portion 16 may extend to substantially fill the area defined by stabilizer portion 20. In certain embodiments, stabilizer portion 20 may be formed in a shape other than the substantially rectangular shape illustrated in FIGS. 1 and 3A. For example, as shown in FIG. 3B, stabilizer portion may be formed in the shape of an arc. As shown in FIG. 3C, in certain embodiments, apparatus 10 may be formed without stabilizer portion 20. As shown in FIG. 3D, in certain embodiments, handle portion 18 may extend from stabilizer portion 20. Although not shown, in certain embodiments, apparatus 10 may include multiple blade portions 16. For example, apparatus 10 may include first and second blade portions 16 offset in opposite directions from an axis through the length of handle portion 18. In any of these embodiments, blade portion 16 may be oriented relative to handle portion 18 at any suitable angle, including angles greater than or equal to zero degrees.

FIGS. 4A and 4B illustrate example upper and lower arches of a person's mouth and example interproximal contact areas from which enamel may be removed. FIG. 3A illustrates a portion of an example upper arch 100, and FIG. 4B illustrates a portion of an example lower arch 102. Upper arch 100 and lower arch 102 include anterior teeth 104. Each tooth 104 includes a protruding portion 106 and a root portion 108. Protruding portion 106 at least partially protrudes from the gum tissue covering the mandible. Root portion 108 extends into the mandible and secures tooth 104 in place.

Tooth 104 includes at least two layers. Enamel 110 forms an outer layer of tooth 104 and is comprised of a hard calcareous substance. An inner layer 112 is comprised of dentin and is very sensitive to decay, disease, and temperature. As described above, however, portions of enamel 110 may be removed from one or more interproximal contact areas 114 using an IER procedure. The removal of portions of enamel 110 from interproximal contact areas 114 may create space, or additional space, between two adjacent teeth 104. Accordingly, the IER procedure may be performed to prevent or treat the overcrowding of teeth 104 associated with malocclusion and avoid the need for tooth extractions. The IER procedure may also be used to recontour one or more teeth 104 to provide a more aesthetically pleasing shape. After portions of enamel 110 are removed at interproximal contact areas 114, teeth 104 may be polished and a protective treatment applied.

Because enamel 110 is a protective layer important to the structure and function of tooth 104, the amount of enamel 110 that may be removed during the IER procedure must be carefully controlled. In certain embodiments, approximately 0.85 mm to approximately 1.13 mm of enamel 110 may be safely removed from each interproximal area 114 of upper arch 100 without producing chronic sensitivity or pain. For example, approximately 1.13, 1.10, 0.91, 0.85, 0.91, 1.10, and 1.13 mm of enamel 110 may be removed from interproximal contact areas 114a-g, respectively. As a result, five medial spaces may be created at interproximal contact areas 114b-f, and a total of approximately 4.87 mm of medial space may be created. If enamel 110 at interproximal contact areas 114a and 114g is also reduced, the total medial space created in upper arch 100 may be approximately 7.13 mm. In certain embodiments, approximately 0.75 mm to approximately 1.00 mm of enamel 110 may be safely removed from each interproximal area 114 of lower arch 102 without producing chronic sensitivity or pain. For example, approximately 1.00, 0.82, 0.75, 0.75, 0.75, 0.82, and 1.00 mm of enamel 110 may be removed from interproximal contact areas 114h-n, respectively. As a result, five medial spaces may also be created at interproximal contact areas 114i-n, and a total of approximately 3.89 mm of medial space may be created. If enamel 110 at interproximal contact areas 114h and 114n is also reduced, the total medial space created in lower arch 102 may be approximately 5.89 mm.

Figure 5:
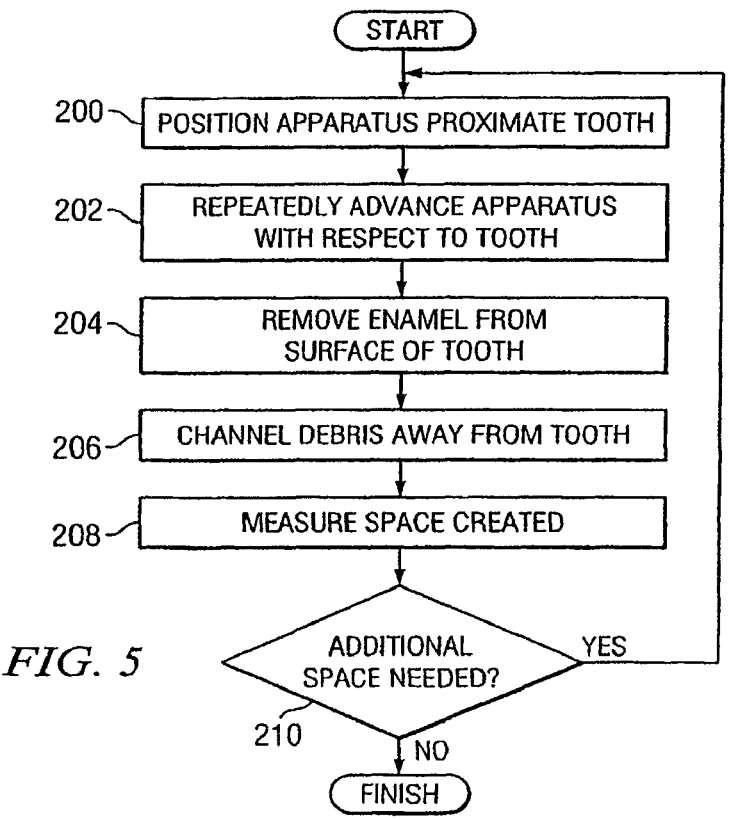
FIG. 5 illustrates an example method for removing enamel from a person's tooth.

FIG. 5 illustrates an example method for removing enamel from a person's tooth 104. The method may include some or all of an IER procedure. At step 200, apparatus 10 is positioned proximate a particular tooth 104 of a person's upper or lower arch 100 or 102. Specifically, abrasive surface 26 may be positioned proximate an interproximal contact area 114 of tooth 104. At step 202, apparatus 10 is repeatedly advanced in opposing directions with respect to tooth 104. Apparatus 10 may be advanced in opposing directions with respect to tooth 104 in a first direction towards the labial surface of tooth 104 and in a second direction towards the lingual surface of tooth 104. As a result, at step 204, abrasive surface 26 may file, saw, or otherwise remove enamel 110 from tooth 104. Enamel 110 may be removed in a similar manner from an adjacent tooth 104. As a result of enamel 110 being removed from one or both adjacent teeth 104, a space or additional space is created between adjacent teeth 104 to prevent or treat overcrowding of teeth 104 associated with malocclusion and avoid the need for tooth extractions. Alternatively or additionally, enamel 110 may be removed from tooth 104 to provide a more aesthetically pleasing shape.

At step 206, as enamel 110 is removed from tooth 104, in certain embodiments debris is channeled away from tooth 104 through one or more apertures 30 formed through blade portion 16 of frame 12. The debris present at interproximal area 114 may include, for example, bits of removed enamel, saliva, blood, and any liquids, chemicals or pastes used in the IER procedure. As a result, such debris may be readily removed from the interproximal area and the area kept cleaner and visibly unobstructed during an IER procedure, without undue interruption.

At step 208, the space created between adjacent teeth 104 is measured. The amount of space to be created depends on the amount of overcrowding, the desired shape and size of the tooth, and other factors particular to the person. At step 210, the clinical professional determines whether additional space is needed. If additional space is needed, the method returns to step 200 for removal of additional enamel 110. The method may continue by repeating steps 200-210 on the same tooth 104 or on an adjacent tooth 104 until the desired amount of space is created. When it is determined at step 210 that additional space is not needed, the method ends.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for removing enamel from a person's tooth to create additional space in the person's mouth to treat or prevent malocclusion, to recontour the tooth to create a more aesthetically pleasing shape, or to treat any other condition that may be improved through the reshaping or resizing of the person's tooth.

Although the present invention has been described above in connection with several embodiments, a plenitude of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. An apparatus for removing enamel from a person's tooth, comprising:
    a one-piece integrally-formed frame comprising a blade portion and a handle portion extending from the blade portion, the frame comprising a first material;
    an abrasive surface on the blade portion, the abrasive surface adapted to remove enamel from the tooth in response to reciprocating movement of the abrasive surface against the enamel of the tooth; and
    a one-piece integrally-formed body substantially covering at least the handle portion of the frame and leaving substantially exposed at least a portion of the blade portion of the frame, the body comprising a second material different from the first material, the body and the handle portion each having a substantially solid cross-section perpendicular to a central axis of the handle portion, the handle portion configured to be inserted into a corresponding opening in a driver mechanism that is adapted to drive reciprocating movement of the blade portion to provide the reciprocating movement of the abrasive surface;
    wherein at least a portion of the body extends through the handle portion of the frame in a direction generally perpendicular to the central axis of the handle portion.

2. The apparatus of claim 1, wherein the blade portion comprises one or more apertures formed through the blade portion and adapted to channel away from the tooth debris resulting from the removal of enamel from the tooth.

3. The apparatus of claim 1, the frame further comprising a stabilizer having a first portion extending from a first end of the blade portion in a first direction generally perpendicular to the central axis, a second portion extending from a second end of the blade portion generally in the first direction, and a third portion extending between the first and second portions to define an opening between the stabilizer and the blade portion, the body substantially enveloping the stabilizer of the frame.

4. The apparatus of claim 1, further comprising the driver mechanism, the driver mechanism comprising an opening adapted to receive an end of the body.

5. The apparatus of claim 1, wherein the at least a portion of the body extending through the handle portion of the frame at least partially fills one or more apertures formed through the handle portion.

6. An apparatus for removing enamel from a person's tooth, comprising:
    a driver mechanism; and
    a tool adapted to removably couple to the driver mechanism, the tool comprising:
        a frame integrally formed from at least a first material, the frame comprising a blade portion and a handle portion extending from the blade portion, the blade portion comprising:
            one or more apertures formed through the blade portion and adapted to channel away from the tooth debris resulting from the removal of enamel from the tooth;
            an abrasive surface extending between two edges of the blade portion and adapted to remove enamel from the tooth in response to reciprocating movement of the abrasive surface against the enamel of the tooth;
        a body integrally-formed from at least a second material different from the first material, the body substantially covering at least the handle portion of the frame and leaving substantially exposed at least a portion of the blade portion of the frame, the body and the handle portion each having a substantially solid cross-section perpendicular to a central axis of the handle portion, the handle portion configured to be inserted into a corresponding opening in the driver mechanism;

wherein the driver mechanism is configured to drive reciprocating movement of the blade portion to provide the reciprocating movement of the abrasive surface against the enamel of the tooth;

wherein at least a portion of the body extends through the handle portion of the frame in a direction generally perpendicular to the central axis of the handle portion.

7. A method for removing enamel from a person's tooth, comprising:

positioning an apparatus for removing enamel proximate the tooth, the apparatus comprising:

a one-piece integrally-formed frame comprising a blade portion and a handle portion extending from the blade portion, the frame comprising a first material;

an abrasive surface on the blade portion, the abrasive surface adapted to remove enamel from the tooth in response to reciprocating movement of the abrasive surface against the enamel of the tooth; and a one-piece integrally-formed body substantially covering at least the handle portion of the frame and leaving substantially exposed at least a portion of the blade portion of the frame, the body comprising a second material different from the first material, the body and the handle portion each having a substantially solid cross-section perpendicular to a central axis of the handle portion, the handle portion configured to be inserted into a corresponding opening in a driver mechanism that is adapted to drive reciprocating movement of the blade portion to provide the reciprocating movement of the abrasive surface;

moving the abrasive surface of the blade portion against the enamel of the tooth in the reciprocating movement; and removing enamel from the tooth in response to the reciprocating movement of the abrasive surface of the blade portion against the enamel of the tooth;

wherein at least a portion of the body extends through the handle portion of the frame in a direction generally perpendicular to the central axis of the handle portion.

8. The method of claim 7, wherein the frame further comprises a stabilizer having a first portion extending from a first end of the blade portion in a first direction generally perpendicular to the central axis, a second portion extending from a second end of the blade portion generally in the first direction, and a third portion extending between the first and second portions to define an opening between the stabilizer and the blade portion, the body substantially enveloping the stabilizer of the frame.

9. The method of claim 7, wherein the blade portion comprises one or more apertures formed through the blade portion and adapted to channel away from the tooth debris resulting from the removal of enamel from the tooth.

10. The method of claim 7, wherein the at least a portion of the body extending through the handle portion of the frame at least partially fills one or more apertures formed through the handle portion.

11. The method of claim 7, wherein the first material comprises a metal and the second material comprises a plastic.

12. The method for of claim 7, wherein:

positioning the apparatus for removing enamel and moving the abrasive surface are preformed using the driver mechanism, the driver mechanism comprising an opening adapted to receive an end of the body.

13. The method of claim 7, wherein the reciprocating movement is substantially linear.

14. The method of claim 7, wherein the reciprocating movement is substantially elliptical.

15. The method of claim 7, wherein the blade portion comprises one or more apertures formed through the blade portion and adapted to channel away from the tooth debris resulting from the removal of enamel from the tooth, each aperture extending from a first surface of the blade portion to a second surface of the blade portion, the first and second surfaces of the blade portion disposed on opposite sides of the blade portion from one another.

16. The method of claim 7, wherein the abrasive surface extends between two edges of the blade portion.

17. The method of claim 7, wherein the abrasive surface lies along an edge of the blade portion.

* * * * *